Figure 1:
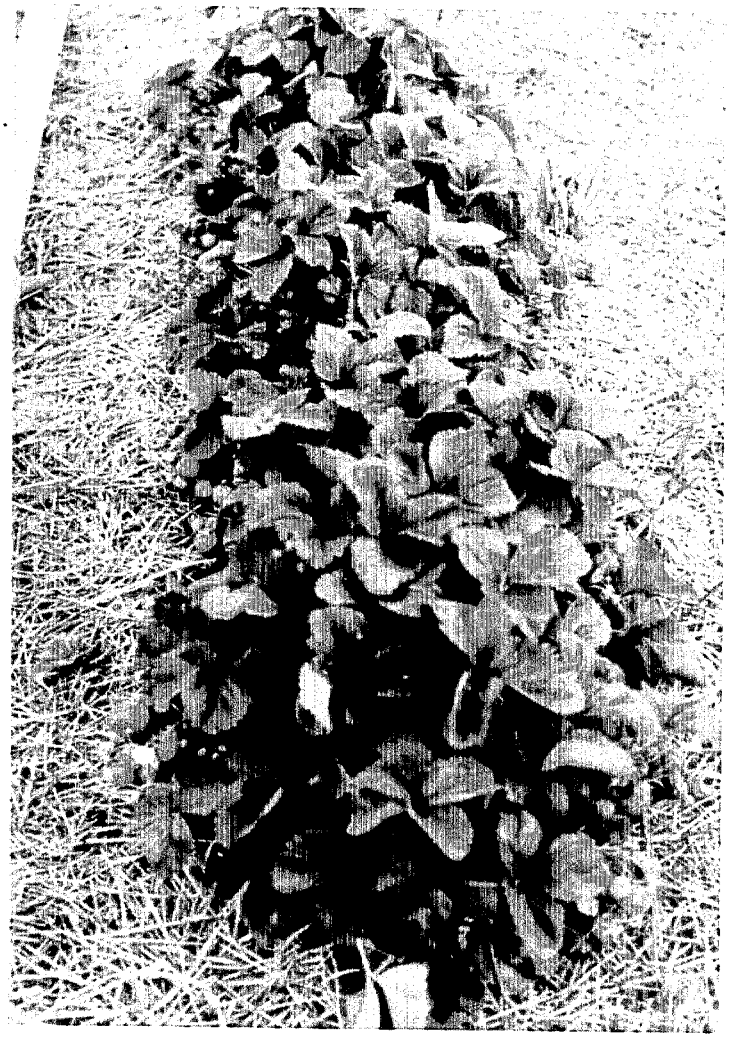

United States Patent [19]

Sanford et al.

[11] Patent Number: Plant 5,897

[45] Date of Patent: Mar. 10, 1987

[54] STRAWBERRY JEWEL

[75] Inventors: John C. Sanford, Geneva, N.Y.; Donald K. Ourecky, Lauderdale Lakes, Fla.; Jack E. Reich, II, Geneva, N.Y.

[73] Assignee: Cornell Research Foundation, Inc., Ithaca, N.Y.

[21] Appl. No.: 751,091

[22] Filed: Jul. 2, 1985

[51] Int. Cl.[4] ..... A01H 5/00

[52] U.S. Cl. ..... Plt./48

[58] Field of Search ..... Plt./48, 49

*Primary Examiner*—James R. Feyrer

[57] ABSTRACT

A strawberry plant which has large fruit, all-around performance and good fruit quality.

3 Drawing Figures

SUMMARY

This invention is a new and distinct variety of strawberry (Fragaria × Ananassa) which is exceptional for its very attractive large fruit, all-around performance and good fruit quality.

ORIGIN

This new cultivar was developed by the small fruits breeding program of the Department of Horticultural Sciences, Cornell University, New York State Agricultural Experiment Station, Geneva, N.Y. The cross was N.Y. 1221 × 'Holiday', which was made in 1969. The specific clone was the sole selection of 292 seedlings from the cross and was selected in June 1971. It has been extensively tested under the number N.Y. 1324. In the fall of 1985, N.Y. 1324 will be named 'Jewel'.

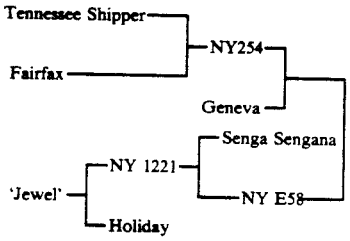

DESCRIPTION

N.Y. 1324 has a moderately vigorous plant growth habit. The trifoliate leaves are borne on erect to semi-erect moderately stout petioles. The petioles are covered with a moderately dense coating of hairs which are generally perpendicular to the petiole epidermis or tending to tilt slightly toward the apical end. The leaflet shape is generally oval to round with approximately straight edges at the base subtending an obtuse angle. Leaflet margins are coarsely toothed. Leaflet upper epidermis is smooth, slightly ridged between lateral veins, dark green and lightly populated with hairs. The lower epidermis is smooth and light green with few hairs.

N.Y. 1324 spreads by means of runners of moderate vigor and number, producing a matted row of medium plant density when that cultural method is used. It also appears well adapted to ribbon-row culture. Propagation is by means of the runner plants and by tissue culture. N.Y. 1324 is adapted to the Northeastern, Great Lakes and Midwestern regions of the United States. It is a hardy and consistent-cropping cultivar resistant to mildew and leaf spot but susceptible to verticillium wilt and red stele.

The fruit of N.Y. 1324 ripens in mid-to-late-midseason. The primary and secondary berries are medium to large, bright red, glossy and blunt-conic to oblate in shape. Tertiary and quarternary berries are smaller and mostly round. Seeds are yellow and set flush with, or slightly raised above, the berry surface. The calyx is medium to large in size, attractive, medium green in color, slightly reflexed and set into a slightly depressed basal surface of the berry. The berry skin is better than average in abrasion resistance. The flesh is slightly firmer than average. The berry color is a bright red, corresponding to Red 46A of The Royal Horticultural Society (London) Colour Chart. The flavor is moderately sweet and slightly acid with some of the aromatic quality of its parent, 'Holiday'. Picking ease is good, with the pedicel tending to snap cleanly a short distance below the calyx.

Table 1 sets forth mean maturity dates based on a 1982 field trial. Traditional cultivars are underlined. Mean date of harvest was calculated on a weighted basis. Means followed by the same letter are not significantly different, based on Waller and Duncan's BSD test, K = 100.

Table 2 sets forth mean subjective fruit skin toughness scores. Traditional cultivars are underlined. Skin toughness was subjectively determined by rubbing the skin of several berries in the hand from each replicate of each genotype. Each plot at each harvest (replicate) was scored independently. Each genotype was rated 1 to 9 with '9' being most resistant to skin abrasion.

Table 3 sets forth mean Instron measurements from 1982 (firmest fruit listed first). Traditional cultivars are underlined. Each genotype mean score reflects the force required for the Instron probe to penetrate the flesh of undamaged berries. Twelve berries were tested of each genotype on the same day of harvest for each harvest date. Means followed by the same letter are not significantly different, based on Waller and Duncan's BSD test, K = 100.

Table 4 sets forth mean berry weight of 29 strawberry genotypes based upon 1982 field trials. Traditional cultivars are underlined. Mean berry weight was determined by dividing total yield per plot by total number of berries per plot. Means followed by the same letter are not significantly different based on Waller and Duncan's BDS test, K = 100.

Table 5 sets forth mean subjective fruit appearance scores. Traditional cultivars are underlined. Berries were rated 1 to 9 with '9' being the most attractive. Each plot at each harvest (replicate) was scored independently. Means followed by the same letter are not significantly different, based upon Waller and Duncan's BSD test, K=100.

Table 6 sets forth mean subjective flavor scores. Traditional cultivars are underlined. Berries were rated 1 to 9 with '9' being best flavor. Each plot at each harvest (replicate) was scored independently. Means followed by the same letter are not significantly different, based on Waller and Duncan's BSD test, K=100.

Table 7 sets forth fruit rot incidence on strawberry cultivars and selections tested in 1978. Shown is the combined score for all rots (Botrytis, soft rots and white mold). Data supplied by Dr. H. S. Aldwinckle, Department of Plant Pathology, New York State Agricultural Experiment Station.

TABLE 1

Mean maturity date of NY 1324 vs. other cultivars.

| Gentoype | Mean Weighted Date of Harvest[1] |
|---|---|
| 'Earlidawn' | June 23 A |
| 'Midland' | June 24 AB |
| NY 1402 | June 25 ABC |
| MDUS 4380 | June 26 BCD |
| 'Lester' | June 26 BCD |
| MDUS 4355 | June 26 BCD |
| NY 1524 | June 26 BCD |
| MDUS 4774 | June 26 BCD |
| 'Catskill' | June 27 CDE |
| NY 1560 | June 27 CDEF |
| 'Honeoye' | June 28 DEFG |
| 'Holiday' | June 28 DEFG |
| NY 1530 | June 28 DEFG |
| MDUS 4579 | June 28 DEFGH |
| 'Raitan' | June 28 DEFGHI |
| NY 1570 | June 29 EFGHIJ |
| NY 1333 | June 29 FGHIJK |
| MDUS 4426 | June 29 FGHIJK |
| NY 1324 - 'Jewel' | June 30 GHIJKL |
| NY 1529 | July 1 HIJKLM |
| NY 1368 | July 1 HIJKLMN |
| NY 1431 | July 1 IJKLMN |
| NY 1406 | July 1 IJKLMN |
| NY 1580 | July 1 JKLMN |
| 'Allstar' | July 1 JKLMN |
| 'Canoga' | July 2 KLMN |
| 'Scott' | July 2 LMN |
| 'Sparkle' | July 3 MN |
| NY 1482 | July 4 N |

TABLE 2

Mean subjective fruit skin toughness scores for NY 1324 and other cultivars.

| Treatment | Replicates | Mean Score* |
|---|---|---|
| NY 1524 | 6 | 7.7 A |
| NY 1529 | 5 | 7.6 AB |
| NY 1324 - 'Jewel' | 5 | 7.4 AB |
| NY 1530 | 6 | 7.2 ABC |
| MDUS 4426 | 5 | 7.0 ABCD |
| NY 1368 | 5 | 6.8 ABCDE |
| MDUS 4579 | 5 | 6.8 ABCDE |
| 'Holiday' | 8 | 6.8 ABCDE |
| NY 1580 | 3 | 6.7 ABCDEF |
| 'Canoga' | 4 | 6.5 ABCDEF |
| 'Scott' | 8 | 6.5 BCDEF |
| 'Lester' | 7 | 6.3 BCDEF |
| 'Allstar' | 4 | 6.2 BCDEFG |
| NY 1333 | 5 | 6.0 CDEFG |
| NY 1406 | 9 | 5.9 DEFG |
| MDUS 4355 | 6 | 5.8 DEFG |
| MDUS 4774 | 5 | 5.6 EFGH |
| NY 1482 | 4 | 5.5 EFGHI |
| NY 1560 | 4 | 5.3 FGHI |

TABLE 2-continued

Mean subjective fruit skin toughness scores for NY 1324 and other cultivars.

| Treatment | Replicates | Mean Score* |
|---|---|---|
| NY 1402 | 5 | 5.2 FGHI |
| NY 1431 | 5 | 5.2 FGHI |
| 'Raritan' | 7 | 5.0 GHI |
| 'Honeoye' | 7 | 4.5 HIJ |
| MDUS 4380 | 6 | 4.3 IJK |
| 'Sparkle' | 5 | 3.8 JK |
| 'Earlidawn' | 8 | 3.7 JK |
| Midland | 7 | 3.0 K |
| NY 1570 | 1 | 2.0 KL |
| 'Catskill' | 7 | 1.1 L |

TABLE 3

Mean firmness measurements for NY 1324 and other cultivars.

| Genotype | Mean puncture force (daltons)* |
|---|---|
| NY 1570 | 65.8 A |
| NY 1529 | 62.7 A |
| MDUS 4579 | 57.6 A |
| MDUS 4774 | 56.4 A |
| NY 1524 | 53.9 AB |
| NY 1530 | 46.9 BC |
| NY 1580 | 46.7 BC |
| NY 1560 | 46.1 BCD |
| 'Holiday' | 45.7 CD |
| 'Canoga' | 44.7 CDE |
| MDUS 4426 | 44.2 CDE |
| 'Allstar' | 39.3 CDEF |
| NY 1431 | 38.3 DEFG |
| 'Scott' | 37.6 EFGH |
| NY 1406 | 35.9 FGHI |
| NY 1324 - 'Jewel' | 33.5 FGHIJ |
| NY 1402 | 32.5 FGHIJ |
| NY 1333 | 30.8 GHIJ |
| NY 1482 | 30.1 GHIJK |
| MDUS 4380 | 30.0 HIJK |
| 'Honeoye' | 28.8 IJK |
| MDUS 4355 | 28.7 IJK |
| 'Lester' | 28.6 IJK |
| 'Midland' | 27.1 JKL |
| NY 1368 | 27.1 JKL |
| 'Raritan' | 25.9 JKL |
| 'Earlidawn' | 25.6 JKL |
| 'Sparkle' | 22.0 KL |
| 'Catskill' | 19.9 L |

TABLE 4

Mean berry weight for NY 1324 and other cultivars

| Genotype | Grams/berry* |
|---|---|
| NY 1524 | 14.4 A |
| 'Canoga' | 13.7 AB |
| 'Allstar' | 13.6 AB |
| NY 1333 | 13.5 ABC |
| MDUS 4426 | 13.4 ABC |
| NY 1431 | 12.6 ABCD |
| NY 1482 | 12.5 ABCD |
| NY 1529 | 11.8 BCDE |
| NY 1570 | 11.5 CDEF |
| NY 1324 - 'Jewel' | 11.3 DEFG |
| 'Lester' | 11.2 DEFG |
| NY 1580 | 11.2 DEFG |
| NY 1406 | 10.9 DEFGH |
| NY 1368 | 10.8 DEFGHI |
| 'Holiday' | 10.7 DEFGHIJ |
| NY 1560 | 10.5 EFGHIJK |
| MDUS 4579 | 10.2 EFGHIJKL |
| 'Honeoye' | 10.0 EFGHIJKL |
| MDUS 4380 | 10.0 EFGHIJKL |
| NY 1402 | 10.0 EFGHIJKL |
| MDUS 4774 | 9.7 FGHIJKL |
| 'Raritan' | 9.3 GHIJKL |
| 'Scott' | 9.1 HIJKL |
| MDUS 4355 | 9.0 HIJKL |
| 'Catskill' | 8.9 HIJKL |

TABLE 4-continued

Mean berry weight for NY 1324 and other cultivars

| Genotype | Grams/berry* | |
|---|---|---|
| NY 1530 | 8.8 | IJKL |
| 'Midland' | 8.7 | JKL |
| 'Sparkle' | 8.6 | KL |
| 'Earlidawn' | 8.3 | L |

TABLE 5

Mean fruit appearance scores for NY 1324 and other cultivars.

| Genotype | Replicates | Mean Score* |
|---|---|---|
| NY 1333 | 5 | 7.6 A |
| 'Lester' | 7 | 7.3 AB |
| NY 1324 - 'Jewel' | 5 | 6.8 ABC |
| NY 1524 | 6 | 6.5 ABCD |
| NY 1530 | 6 | 6.3 ABCD |
| MDUS 4355 | 6 | 6.3 ABCDE |
| 'Honeoye' | 7 | 6.3 ABCDE |
| NY 1529 | 5 | 6.2 ABCDEF |
| MDUS 4380 | 6 | 6.2 BCDEF |
| 'Scott' | 8 | 6.1 BCDEF |
| NY 1368 | 5 | 6.0 BCDEF |
| NY 1560 | 4 | 5.8 CDEF |
| 'Raritan' | 7 | 5.7 CDEFG |
| 'Allstar' | 4 | 5.5 CDEFG |
| 'Canoga' | 4 | 5.5 CDEFG |
| 'Holiday' | 8 | 5.5 CDEFG |
| NY 1431 | 5 | 5.4 CDEFG |
| NY 1530 | 3 | 5.3 CDEFG |
| NY 1482 | 4 | 5.3 DEFG |
| NY 1402 | 5 | 5.0 EFG |
| NY 1406 | 9 | 4.9 FG |
| MDUS 4774 | 5 | 4.8 FG |
| 'Earlidawn' | 8 | 4.6 G |
| MDUS 4426 | 5 | 4.2 G |
| MDUS 4579 | 5 | 4.0 G |
| 'Midland' | 7 | 4.0 G |
| 'Sparkle' | 5 | 3.4 G |
| NY 1570 | 2 | 3.0 GH |
| 'Catskill' | 7 | 1.9 H |

TABLE 6

Mean flavor scores for NY 1324 and other cultivars.

| Treatment | Replicates | Mean Score* |
|---|---|---|
| 'Lester' | 7 | 6.3 A |
| NY 1570 | 2 | 6.0 AB |
| NY 1529 | 5 | 6.0 AB |
| NY 1324 - 'Jewel' | 5 | 5.8 AB |
| 'Holiday' | 8 | 5.8 AB |
| NY 1368 | 5 | 5.6 AB |
| NY 1560 | 4 | 5.5 AB |
| 'Sparkle' | 5 | 5.4 AB |
| NY 1524 | 6 | 5.3 AB |
| 'Raritan' | 7 | 5.3 AB |
| 'Honeoye' | 7 | 5.1 AB |
| 'Allstar' | 4 | 5.0 AB |
| 'Canoga' | 4 | 5.0 AB |
| MDUS 4380 | 6 | 5.0 AB |
| 'Scott' | 8 | 4.9 AB |
| NY 1530 | 6 | 4.8 AB |
| MDUS 4355 | 6 | 4.8 AB |
| MDUS 4426 | 5 | 4.8 AB |
| NY 1333 | 5 | 4.8 AB |
| NY 1431 | 5 | 4.8 AB |
| NY 1580 | 3 | 4.7 AB |
| MDUS 4774 | 5 | 4.6 B |
| NY 1402 | 5 | 4.6 B |
| 'Midland' | 7 | 4.4 B |
| NY 1406 | 9 | 4.2 B |
| NY 1482 | 4 | 4.0 B |
| 'Catskill' | 7 | 4.0 B |
| MDUS 4579 | 5 | 3.8 B |
| 'Earlidawn' | 8 | 3.8 B |

TABLE 7

Mean fruit rot scores for NY 1324 and other cultivars.

| Cultivar or Selection | Mean Number Rotted Per 12 | Reps. |
|---|---|---|
| Earlidawn | 11.7 A | 3 |
| NY 1476 | 11.2 A | 5 |
| NY 1402 | 11.2 A | 5 |
| Vibrant | 10.6 AB | 5 |
| Veestar | 10.6 AB | 5 |
| NY 1477 | 10.4 AB | 5 |
| NY 1515 | 10.0 ABC | 3 |
| NY 1531 | 9.8 ABC | 5 |
| NY 1530 | 9.8 ABC | 5 |
| NY 1415 | 9.8 ABC | 5 |
| NY 1287 | 9.8 ABC | 5 |
| NY 1475 | 9.4 ABCD | 5 |
| V6747R6 | 9.4 ABCD | 5 |
| Holiday | 9.4 ABCD | 5 |
| MD 4359 (Lester) | 9.2 ABCDE | 5 |
| NY 1529 | 9.0 ABCDEF | 5 |
| NY 1527 | 9.0 ABCDEF | 4 |
| NY 1261 | 9.0 ABCDEF | 5 |
| Surecrop | 9.0 ABCDEF | 5 |
| NY 1366 | 8.0 ABCDEFG | 3 |
| NY 1264 | 8.0 BCDEFG | 4 |
| Tenira | 7.4 CDEFG | 5 |
| NY 1285 | 7.2 CDEFGH | 5 |
| NY 1524 | 7.0 CDEFGH | 3 |
| NY 1431 | 7.0 CDEFGH | 5 |
| NY 1368 | 7.0 CDEFGH | 5 |
| NY 1333 | 6.8 CDEFGH | 5 |
| NY 1362 (Canoga) | 6.6 DEFGH | 5 |
| NY 1384 | 6.4 EFGH | 5 |
| Guardian | 6.2 FGH | 5 |
| NY 1324 - 'Jewel' | 5.8 GH | 5 |
| NY 1406 | 5.2 GH | 5 |
| NY 1404 | 4.8 GH | 5 |
| NY 1409 (Honeoye) | 4.4 H | 5 |

Combined score for all rots (Botrytis, soft rots, and white mold). Data supplied by Dr. H. S. Aldwinckle, Department of Plant Pathology, New York State Agricultural Experiment Station.

DESCRIPTION OF PHOTOGRAPHS

The following describes the accompanying photographs, documenting the unique features characterizing this new culture.

FIG. 1. Ribbon-row of 'Jewel' in second year from planting. Plot is a single line of plants spaced 6" apart in the row and all runners kept removed.

Figure 2:
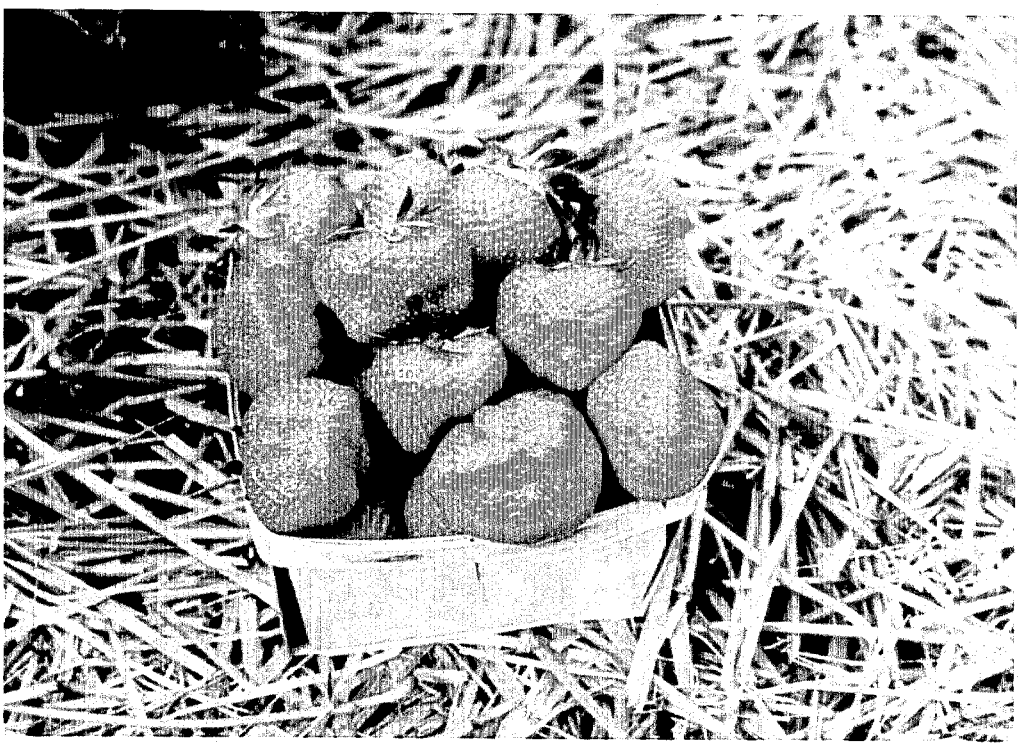

FIG. 2. Fruit of 'Jewel' in a one-quart box. Note size of fruit, wedge-conic shape and glossy, attractive appearance.

Figure 3:
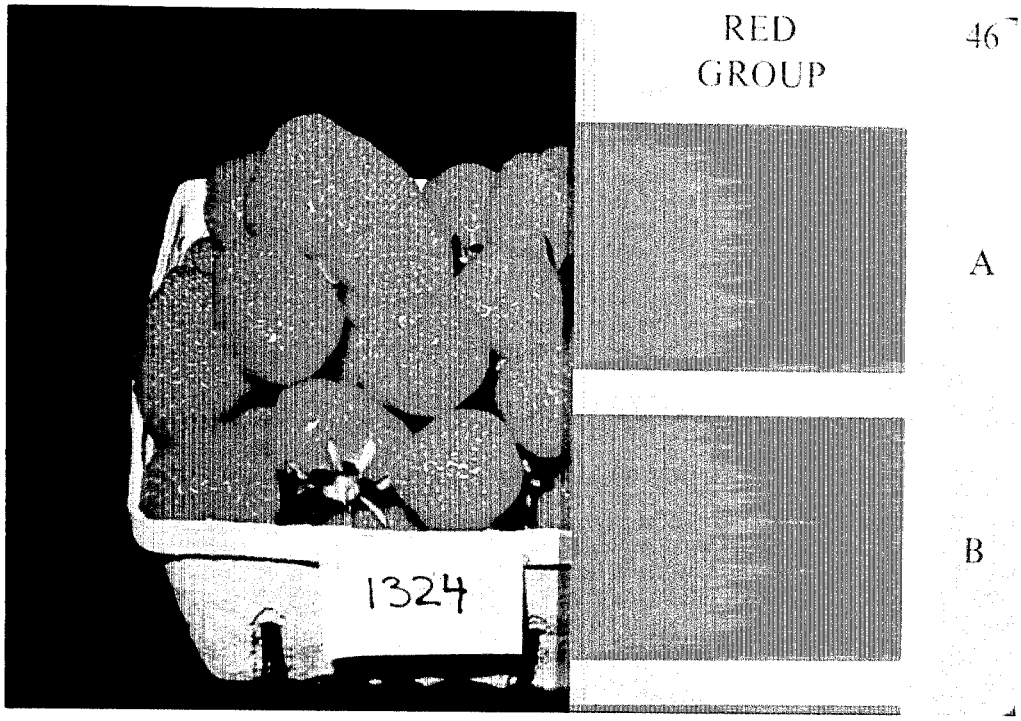

FIG. 3. Comparison of the fruit of 'Jewel' with the corresponding color from The Royal Horticultural Society Colour Chart.

MERITS

The most outstanding feature of N.Y. 1324 is its well-balanced, all-around performance. It combines good fruit size (Table 4), attractiveness (Table 5), quality (Table 6), tough skin (Table 2) and moderately firm flesh (Table 3). In addition, the fruit of N.Y. 1324 are better than average in resistance to various fruit rots (Table 7). Also, N.Y. 1324 has consistently been rated above most other cultivars in frozen fruit taste panel trials.

The plants of N.Y. 1324 have good hardiness and wide regional adaptation. Thirteen of sixteen cooperative testers from different regions rated N.Y. 1324 as above-average to outstanding for all of the following traits: yield, flavor, fruit size, appearance, firmness, keeping quality and foliar disease resistance.

We claim:

1. The new and distinct variety of strawberry herein described and illustrated and identified by the characters enumerated above.

* * * * *